(12) United States Patent
Weisenthal

(10) Patent No.: US 8,192,949 B2
(45) Date of Patent: Jun. 5, 2012

(54) MICROAGGREGATES INCLUDING ENDOTHELIAL CELLS

(76) Inventor: Larry M. Weisenthal, Huntington Beach, CA (US)

(*) Notice: Subject to any disclaimer, the term of this patent is extended or adjusted under 35 U.S.C. 154(b) by 626 days.

(21) Appl. No.: 11/639,873

(22) Filed: Dec. 15, 2006

(65) Prior Publication Data

US 2007/0190648 A1 Aug. 16, 2007

Related U.S. Application Data

(60) Provisional application No. 60/751,127, filed on Dec. 16, 2005.

(51) Int. Cl.
*G01N 1/28* (2006.01)
*G01N 1/30* (2006.01)
*C12Q 1/00* (2006.01)

(52) U.S. Cl. .............. 435/40.5; 435/4; 435/29

(58) Field of Classification Search ............ 435/40.5, 435/4, 29
See application file for complete search history.

(56) References Cited

U.S. PATENT DOCUMENTS

| | | |
|---|---|---|
| 2002/0150879 A1 | 10/2002 | Woltering et al. |
| 2004/0146990 A1 | 7/2004 | Mather et al. |
| 2004/0171089 A1 | 9/2004 | Spruce et al. |
| 2004/0259177 A1* | 12/2004 | Lowery et al. ............. 435/7.23 |

FOREIGN PATENT DOCUMENTS

EP 1 506 998 2/2005

OTHER PUBLICATIONS

Ljung et al. 1989. Cell dissociation techniques in human breast cancer—Variations in tumor cell viability and DNA ploidy. Breast Cancer Research and Treatment 13:153-159.*
Auerbach et al., Cancer Metastasis Rev. (2000) 19:167-172.
Ince et al., J. Natl Cancer Inst (2005) 97:981-989.
Staton et al., Int. J. Exp. Path (2004) 85:233-248.
Willett et al., Nature Med (2004) 10:145-147.
International Search Report and Written Opinion for PCT/US06/47954, mailed Sep. 22, 2008, 6 pages.
Gulec et al., Annals of Surgical Oncology (2004) 11(1):99-104.
Supplementary European Search Report for EP 06848923.6, mailed Apr. 22, 2009, 8 pages.
Woltering et al., Annals of Surgery (2003) 237(6):790-798.
Weisenthal et al., Cancer Research (1983) 43:749-757.
Weisenthal et al., "Platinum Resistance Determined by Cell Culture Drug Resistant Testing (CCDRT) Predicts for Patient Survival in Ovarian Cancer" Internet Dec. 8, 2003, http://www.weisenthal.org/w_ovarian_cp.pdf [retrieved Jan. 15, 2010].
Office Action from European Patent Application No. 06848923.6, dated Jun. 28, 2010, 5 pages.

* cited by examiner

*Primary Examiner* — Taeyoon Kim
(74) *Attorney, Agent, or Firm* — Morrison & Foerster LLP

(57) ABSTRACT

Microaggregates which mimic the native environment of cells contained in biopsied tissue are used to assess and predict the effects of various treatments on the viability of cell types contained in the microaggregate.

10 Claims, 8 Drawing Sheets

Cells in Microcluster

CD31 cytoplasmic staining confirms morphological identification of microcapillary cells in tumor microcluster Negative Control Living cells in culture, NOT exposed to anti-VEGF drug. Intact membranes of undamaged microcapillary cells exclude vital dye - no visible staining.

Leaky membranes of dead/ dying micro-capillary cells admit vital dye which then extrudes into adjacent spaces during alcohol-based counterstaining. Tumor cells are not harmed by anti-VEGF drug.

40x

40x

200x

400x

Control 100x

Bevacizumab 100x

Control 100x (Annotated)

Bevacizumab 100x (Annotated)

Control 200x

Bevacizumab 200x

Control 200x (Annotated)

Bevacizumab 200x (Annotated)

MICROAGGREGATES INCLUDING ENDOTHELIAL CELLS

CROSS-REFERENCE TO RELATED APPLICATION

This application claims benefit under 35 U.S.C. §119(e) of U.S. provisional application Ser. No. 60/751,127 filed 16 Dec. 2005. The contents of this application are incorporated herein by reference.

TECHNICAL FIELD

The present invention relates to the study of the viability of tissue microvasculature in microaggregates that maintain a native configuration and, more particularly, to the study of methods to destroy, disrupt, or promote the survival and/or proliferation of microvasculature in said microaggregates. The invention is particularly useful in assessing the effect of candidate drugs for treatment of tumors, especially those that specifically and directly inhibit the growth of neovasculature.

BACKGROUND ART

When tissues (normal and neoplastic) increase in size, they require the formation of microcapillaries (angiogenesis) to provide nourishment to sustain their growth. Constituents of these microcapillaries include most prominently endothelial cells, but also associated mesenchymal cells, fibroblasts, smooth muscle cells, and pericytes. Angiogenesis is important in normal processes, such as wound healing, but also in diseases such as cancer, psoriasis, diabetes, rheumatoid arthritis, and age-related macular degeneration.

There is a need for improved methods for studying microcapillaries in vitro in both normal and diseased tissues. A summary of presently known methods is provided in Staton, et al., "Current Methods for Assaying Angiogenesis in vitro and in vivo," *Int J Exp Path* (2004) 85:233-248. In vivo models are useful but cumbersome. In vitro models are less cumbersome but also more artificial and less relevant.

In particular, there is a need for improved methods to predict the activity of anti-cancer drugs and other treatments which target the microvasculature of tumors. For example, bevacizumab (Avastin®) is an FDA-approved anti-cancer drug which targets the microvasculature of tumors. The wholesale cost of Avastin® is more than $40,000 for 10 months of treatment; yet only a relatively small percentage of patients derive substantial benefit. As stated by Ince, et al., "Association of k-ras, b-raf, and p53 Status with the Treatment Effect of Bevacizumab," *J Natl Cancer Inst* (2005) 97:981-989, the identification of biomarkers that may predict which patients are most likely to respond to such treatment is of considerable interest.

The most commonly used in vitro methods involve isolating and culturing endothelial cells. Once the cells have been cultured, the effect of drugs (or other perturbations) may be studied, using a variety of cell proliferation and/or cell death endpoints. Examples of cell proliferation endpoints include radioactive thymidine incorporation, cell counting, BrdU incorporation, and colony formation. Examples of cell death endpoints include measurement of cellular ATP, mitochondrial reduction of MTT, metabolism and intracellular trapping of fluorescein diacetate (and loss thereof), loss of cell membrane integrity by dye exclusion, and more specific measurements of apoptosis, such as TUNEL assay or caspase expression. In some cases, previously-isolated endothelial cells have been co-cultured with previously-isolated other cells, and differential effects of drugs on the different cell populations have been studied.

Other in vitro methods are based on organ cultures. For example, see Staton, et al., supra). These include rat aortic ring, chick aortic arch, porcine carotid artery, placental vein disk, and fetal mouse bone explant.

Cell culture assays have clear disadvantages. First, they depend upon the isolation and culture of viable endothelial cells, which can be problematic particularly in the case of fresh human tumors. Once isolated and cultured, they are removed from the native microenvironment, in which factors released by the tumor cells (or normal cells, in the case of normal tissues) are not present. Although isolated tumor cells (or normal cells) could, in principle, be co-cultured, this would not approximate the spatial relation and cell-cell interactions existing in vivo. Existing organ cultures have similar limitations, in that, as stated by Staton, et al., supra, "the model in not truly representative of the microvascular environment encountered in tumor growth as the large number of different factors released by the tumor cells and the tumor cells themselves are not present." See also Auerbach, et al., "Angiogenesis assays: problems pitfalls," *Cancer Metastasis Rev.* (2000) 19:167-172.

Non-cell culture, non-organ culture, approaches to studying and predicting the effects of bevacizumab have been disclosed by Ince, et al., *J Natl Cancer Inst* (2005) supra. Ince attempted to correlate k-ras, b-raf, and p53 status with treatment effect of bevacizumab, but concluded that they "did not identify any subgroup of metastatic colorectal cancer patients who were more likely to respond to bevacizumab therapy." In their discussion, Ince, et al., noted that "To date, few studies have assessed the potential utility of biomarkers in predicting which patients are more likely to respond to antiangiogenic therapy in the clinic" and that no markers had been yet found to be predictive of clinical benefit. These authors suggested that "biomarkers which summarize the effects of all angiogenic regulators may better predict patient outcome than the analysis of a single growth factor or signal induction pathway," but did not suggest any in vitro methods for this purpose. Instead, they noted ongoing work in which patients themselves are used as experimental models for predicting their own outcomes.

In these studies bevacizumab (and/or other treatments) are administered to the patient on a trial basis and then "early" treatment effects are assessed by means of external diagnostic scanning (e.g., MRI) and/or post-treatment tumor biopsies, with histopathologic evaluation of treatment effects (e.g., Willett, et al., *Nature Med* (2004) 10:145-147. This approach has many obvious disadvantages, including expense of treatment, exposure of patient to potential toxicity of ultimately ineffective therapy, and the expense of diagnostic studies (e.g., MRI). Such studies also lack of ability to test multiple different treatments simultaneously without risk to the patient as is possible with in vitro methods.

Clearly, the lack of useful in vitro models in which to study human tumor microvasculature is an obstacle to the identification and development of newer, more effective treatment approaches targeting tumor microvasculature.

DISCLOSURE OF THE INVENTION

The compositions and methods of the invention are able to detect and/or quantify changes, e.g., viability changes, in the microvasculature of microaggregates of cells isolated from biopsied neoplastic or normal tissues in response to chemical, biological, and/or physical treatments. The treatments are generally administered to the microaggregates that have been isolated because these microaggregates to mimic in vivo conditions. It is also sometimes useful to utilize these isolates to determine the results of treatments that have been administered in vivo.

The observed microvascular and other cellular changes serve as tests to predict the in vivo activity of the tested treatments, and thus, the methods of the invention, while able to detect specific effects on endothelial cells, also permit the observation of effects of the same or concomitantly administered treatment on the surrounding cells. Thus, a particular drug may affect both endothelial cells and the surrounding cells.

These methods may be used to aid in the discovery and/or development of novel or investigational treatments.

Thus, in one aspect, the invention is directed to an isolated microaggregate comprised of at least viable endothelial cells and natively surrounding viable non-endothelial cells, which microaggregate is displayed on a surface suitable for microscopic observation. The microaggregate is prepared from biopsied tissue and represents a microcosm of the tissue (tumor or normal) from which the biopsy was obtained. The viable endothelial cells are present, therefore, in their native configuration that may include tumor cells (in the case of cancer), normal tissue cells, connective tissue cells, inflammatory cells and other natively associated cells. The endothelial cells may include intact segments of microcapillaries themselves including endothelial cells and other cells which are constituents of capillaries. The microaggregates may contain several to tens to hundreds to thousands of cells.

The microaggregates may be cultured in standard tissue and/or organ culture apparatus, in standard tissue/and or organ culture media, containing appropriate nutrients and supplements) for a period of hours to days to weeks. The culturing provides an opportunity to assess the effect of various treatments or factors or protocols on both the endothelial cells contained in the microaggregate and the surrounding cells as well.

In another aspect, the invention relates to a method to prepare isolated microaggregates comprised of at least viable endothelial cells and natively surrounding viable non-endothelial cells which can then be sedimented onto a surface suitable for microscopic observation. This method comprises subjecting a minced biopsy sample to a series of centrifugation steps referred to herein as "quickspin." This is described in more detail below. In each step, the sample is brought to being subjected to a force of 50-500×g and then immediately allowed to return to 1×g to obtain a cell cluster pellet and a supernatant. The supernatant is removed and the pellet resuspended and the process is repeated until a suitable isolated microaggregate is formed.

The microaggregates can then optionally be cultured as described above or can immediately be sedimented onto a surface for microscopy. Alternatively, the initial preparation of microaggregates can be treated with an indicator dye that is excluded from viable cells, or treatment with the dye can be performed during or after culturing, but, in any case, prior to sedimenting the microaggregates onto the surface. In still another alternative, the above indicator dye may be applied after sedimentation onto the surface has occurred.

In a preferred aspect, the invention provides a method to identify an agent that specifically effects the death of endothelial cells which comprises treating isolated microaggregates as prepared above with a candidate agent, allowing sufficient time for the agent to exert an effect, treating the microaggregate with a first indicator that is excluded from viable cells and observing the uptake or lack of uptake of the indicator by cells in the microaggregate whereby an agent that affects uptake of said indicator in endothelial cells but not the surrounding cells is identified as an agent that specifically effects the death of endothelial cells.

Various other aspects of the invention will be apparent from the following description.

MODES OF CARRYING OUT THE INVENTION

The invention, in one aspect, is directed to a method to study the microvascularity of viable tissue in microaggregates that mimic native conditions. The method includes isolation of microaggregates or clusters of cells from biopsied tissue. These clusters represent a microcosm of the tissue (tumor or normal) from which the biopsy was obtained, including tumor cells (in the case of cancer), normal tissue cells, connective tissue cells, inflammatory cells, and, in some cases, intact segments of microcapillaries, containing endothelial cells and other cells which are capillary constituents. The clusters may contain several to tens to hundreds to thousands of cells. The clusters may then be cultured in standard tissue and/or organ culture apparatus, in standard tissue/and or organ culture media (containing appropriate nutrients and supplements) for a period of hours to days to weeks. Cells may be exposed to various treatments presumed to have potential effects on the microcapillaries and/or constituent cells of the microcapillaries prior to biopsy (i.e., in the patient), following biopsy but before cell culture, or during the culture period. Treatments may injure or kill or promote or enhance the survival and/or proliferation of the microcapillaries and/or constituent cells.

Following these treatments, the presence and/or viability of cells in the microaggregate may be assessed by adding a first indicator substance or stain that labels non-viable cells (for example, fast green dye, fluorescein diacetate, etc.), and, if desired, a second indicator (that labels viable cells, for example, a cytologic or histologic stain, such as hematoxylin/eosin (H/E)). Sedimentation or deposition of the clusters onto a surface such as a microscope slide (for example but not limited to cytocentrifugation, is performed before or after one or more stains is added. When desired the addition of the first indicator may be omitted. When desired, a third indicator (e.g., an immunocytochemical stain to an antigen such as CD31) may be added to aid in the identification of specific cells within the cluster. The surface is then examined and the status of the cells assessed.

Figure 1A:
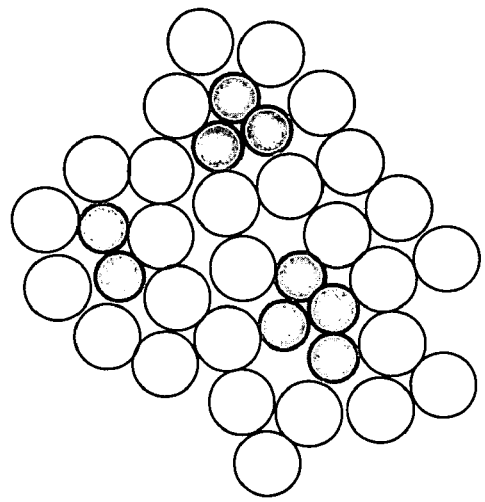
FIGS. 1A-1C are diagrammatic descriptions of the microaggregates of the invention.
Figure 1B:
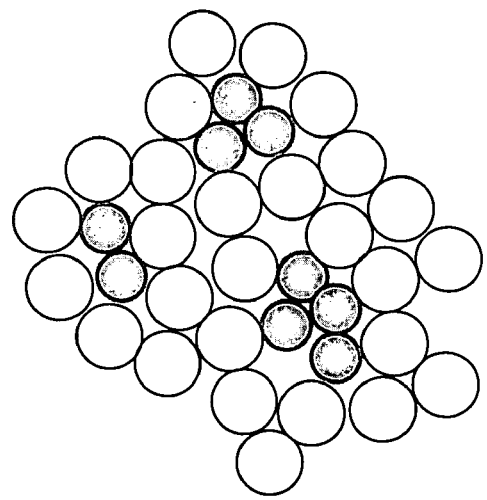
Figure 1C:
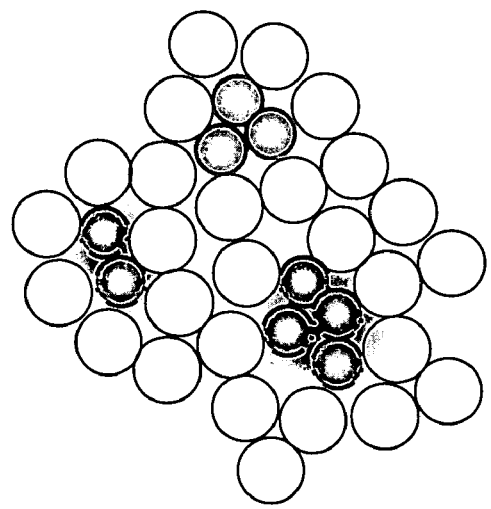

The character of the microaggregates that are the subject matter of the present invention is shown diagrammatically in FIGS. 1A-1C. In each case, a microcluster of cells is shown prepared as described herein from biopsied tissue. In FIG. 1A, endothelial cells are confirmed present by staining with CD31 and these cells are shown as shaded surrounded by accompanying cells shown as open circles. In the illustrative diagrams of FIGS. 1A-1C, the intended treatment is exposure to an anti-VEGF drug. FIG. 1B shows a negative control where no treatment was supplied, and as shown, when this cluster is exposed to a dye excluded from living cells but not excluded from dead cells, no change in appearance occurs, since the cells have not been damaged. However, in FIG. 1C, where the cluster has been exposed to an anti-VEGF drug, the dye is taken up by the endothelial cells and they are therefore identified as affected by the drug. The surrounding cells, shown as open circles, do not take up the dye and remain the same.

Thus, by preparing the clusters shown, the ability of individual endothelial cells to show a response to the anti-VEGF drug, used for illustration, is demonstrated.

The invention method thus, in one aspect, comprises isolating cell microaggregates interlaced with capillary-associated cells and utilizing an indicator method capable of recognizing selective alterations in capillary-associated cells in contrast to the non-capillary associated cells comprising the generally greater part of the cell microclusters.

The invention permits detection of microvascular viability in cell microaggregates pre-culture and/or post-culture derived from neoplastic and/or normal tissues where the method comprises:
  isolating microaggregates of biopsied cells by means of "quickspins";
  transferring the microaggregates onto surfaces, such as microscope slides;
  staining the microaggregates with dyes, such as fast green stain and/or H/E; and
  scoring viability of microcapillary-associated and/or surrounding cells.

The stains may be applied before or after transfer onto the surface.

During the culture period, cells may be exposed to various treatments presumed to have potential effects on the microcapillaries and/or constituent cells of the microcapillaries and/or surrounding cells. Treatments may be studied that injure or kill the relevant observed cells or treatments may be studied that promote or enhance the survival and/or proliferation of the microcapillaries and/or constituent cells.

In more detail, following these treatments, the presence and/or viability of the cells in the microaggregate may be assessed by first adding a first indicator substance which selectively labels cells that are non-viable (for example, fast green dye, fluorescein diacetate, etc.), followed by sedimentation or deposition of the microclusters onto a microscope slide (for example by a method exemplified, but not limited to, cytocentrifugation), followed by, when advantageous, exposure of the clusters on the slide to a second indicator (for example, a cytologic or histologic stain, such as hematoxylin/eosin). This indicator is not excluded by viable cells and serves as a contrast agent to enhance the visibility of the first indicator. Alternatively, the first indicator may be added after deposition of the cluster. Also, when desired, the addition of the first indicator substance may be omitted. Additionally, when desired, a third indicator substance (e.g., an immunocytochemical stain to an antigen such as CD31) may be added to aid in the identification of specific cells within the cluster. Following the above, the surface is then examined microscopically and the status of the microvasculature and/or other surrounding cells is assessed, scored, and/or quantified by "manual" methods, i.e., by a trained observer and/or with the use of an instrument, such as an image analyzer. In addition to effects on the cells in the microvasculature, drug effects on the other cells within the cluster (e.g., tumor cells) may be simultaneously or metachronously examined.

Either or both normal tissues and tumor tissues are tested by the invention method, with drug or other treatment effects may be differentially determined on capillary associated cells versus other cells present in the clusters.

The viability of the various cells could also be determined shortly after biopsy without a period of cell culture. Capillary and other cell viability could be measured, for example, in patients who had received no treatment, or in patients who had received clinical treatment some period of time before biopsy (performed with a needle or other biopsy instrument).

As used herein, "treatment" refers to any deliberate change effected in the environment of the microaggregate. Most commonly, the treatment is adding to a culture of the microaggregates a pharmaceutical agent, such as a chemotherapeutic drug. However, other treatments might include changes in temperature, pH, culture conditions and composition, such as change in the nutrients supplied, or a combination of various chemical compounds, such as small molecules or peptides. Treatments may also include inclusions of chemokines or any other deliberately administered protocol.

As used herein, "microaggregates" refers to groups of cells that effectively mimic the native environment of the cells being tested therein. In one embodiment, the effect of treatments on endothelial cells is of interest. In this case, the microaggregate will include at least endothelial cells, and sufficient surrounding cells to provide a surrogate for the native environment of said cells. In theory, only one endothelial cell and an accompanying cell might be included. In the present application, "microaggregates", "microclusters", and "clusters" are used interchangeably.

PREPARATION A

Tumor and/or Normal Tissue Specimens

Fresh biopsies or fluid aspirates are obtained from patients with cancer or other illnesses or from normal donors.

Specimens are typically submitted for conduct of the invention method via the anatomic pathology laboratories of the submitting hospitals, or, in some cases, directly from the operating room or a surgeon/physician office. Solid tumor specimens (not exposed to fixatives or frozen) are placed in cold transport medium ($CO_2$-independent medium, InvitroGen/GIBCO, Grand Island, N.Y., supplemented with penicillin/streptomycin, amphotericin B, insulin/selenium/transferrin, and 10% low endotoxin, heat inactivated fetal bovine serum). Specimens are then placed in sturdy Styrofoam® shipping boxes, containing 350 gm blocks of "blue ice" frozen to minus 20 degrees Celsius. These are then shipped either by a priority overnight delivery service or via local land courier. Fluid specimens are mixed well to suspend cell clusters and then poured into sterile 500 ml polypropylene transport bottles. Ten to fifteen units of heparin sulfate are added per ml of fluid submitted.

Copies of the official histopathology reports from the submitting hospitals should be received.

The following examples are offered to illustrate but not to limit the invention.

Example 1

Isolation of Tumor Cell Microaggregates

Solid tumors are minced to pieces smaller than 1 mm (small enough to be aspirated into a standard disposable 10 ml pipette) with high quality curved surgical scissors. Medium in which said tumors may have been transported is reserved, along with the supernatant from the tissue mince. Scissor-minced tumor pieces are digested with collagenase/DNase in RPMI-1640 containing antibiotics and 10% fetal calf serum. Specimens are digested in 50 ml disposable polypropylene centrifuge tubes, assisted by gentle mixing with plastic-coated, magnetic stirring bars over a stirring plate. Specimens are thusly mixed until complete gross digestion has taken place—typically about 2-3 hours for a 1-3 gram specimen. Cytospin slides are then prepared from all cell fractions (transport medium, supernatant from tissue mince, and enzyme digestate), and stained with fast green-H/E, as described previously (Weisenthal, et al., "A Novel Dye Exclusion Method for Testing in vitro Chemosensitivity of Human Tumors," Cancer Res. (1983) 43:749-757).

Fluid specimens are centrifuged in their entirety to collect all cells in the specimen. Cells are then resuspended in the above RPMI-1640-based medium and cytospins are prepared as described above.

Viable microaggregates are enriched from medium containing a mixture of microclusters that exist in the minced, digested tissue along with single cells, normal cells, red blood cells, dead cells, and debris by means of "quickspins." Quickspins consist of repeated very brief centrifugations at 50-500× g, in which the centrifuge tube is first mixed by moderate hand-shaking, placed in a standard, room temperature, preparatory centrifuge, and then accelerated to the desired speed (determined for each centrifuge by empiric trials) and then immediately turned off once the centrifuge has reached the desired speed and then allowed to coast to a stop. Following each quickspin, the supernatant is aspirated and reserved, while the cell cluster pellet is collected and resuspended for repeated centrifugation steps.

This process is monitored by preparing cytospins of the resuspended cell clusters, until fractions containing 90% of the viable cells as cell clusters are obtained. When it is not possible to achieve this ideal, fractions containing the highest possible percentage of cells in clusters are combined.

The concentrations of cell clusters are adjusted so that approximately 25% of the area of the cytospin cellular "disk" ("spot") is comprised of reddish-pink (viable) tumor cell clusters, and 75% is comprised of empty space. This cell concentration is of critical importance, as overplating and underplating may produce artifactual drug resistance and sensitivity results and/or may adversely affect survival of the cell clusters during subsequent culture. Assay conditions must be standardized, as results are based on comparison with a universe of comparison assays, as described below.

To normalize the results, "day zero" slides are prepared, depicting the condition of the cells not exposed to treatment at the beginning of the assays, and "end culture" slides of negative control (non-exposed cells) are also prepared. So that factors independent of the effect of treatment may be factored out, both day zero and end culture slides are subjectively scored as to (1) percentage of total viable tumor cells (or other cells of interest) which are in clusters (as opposed to being single cells); (2) average density of cell clusters, where "loose" clusters have clear spaces between the cells following cytospin centrifugation, "medium" clusters do not contain clear spaces between cells but are flattened to a two dimensional appearance, and "tight" clusters maintain a three dimensional appearance following cytospin centrifugation, and (3) median two dimensional area of the cell clusters, as measured with an ocular micrometer. These factors all influence the ability of the treatment to reach the relevant cells, so they must be taken into account when comparing results. It may be advantageous to loosen "tight" cultures so as to permit easier penetration by macromolecules, such as antibodies. This can be effected by adding enzymes such as hyaluronidase to the digest. In addition to these cluster measurements, slides are subjectively scored to determine the ratio of viable cells in the end of culture relative to the number of viable cells at the beginning of culture (zero hours or "day 0").

Example 2

Culture/Treatment Step

To test the effect of treatment, such as effect of a drug, the cell cluster suspensions are mixed with 10% (volume/volume) drug solution or vehicle control (most typically 0.9% NaCl). Final volume of cell suspension/drug solution (or vehicle) plated for culture is 0.12 ml. Culturing is in polypropylene round bottom, 96-well culture dishes in a humidified 37° C. incubator for a standardized duration of time.

Stock solutions are generally prepared at ten times the desired concentrations, aliquotted into single-use, 0.5 ml conical polypropylene tubes, and frozen at −70° C. prior to use. Some drugs are maintained at refrigerator temperature, according to manufacturer's recommendations.

Cells are cultured with the index concentration of each drug and, if desired, with dilutions of the index concentration, where the index concentration is determined from training set assays or from the literature. Negative controls generally consist of 0.9% NaCl, and/or the vehicle in which a drug of interest is dissolved. For tumor samples, positive controls are supplied 100 µg/ml of cisplatin plus 1 µg/ml of anguidine (obtained from the National Cancer Institute). Replicate 96-well plates are tested.

Example 3

In Situ Microcapillary Viability Assay (ISMCVA)

On the fourth culture day, 0.010 ml of Alamar Blue dye solution (Trek Diagnostic Systems, Westlake, Ohio) is added to all culture wells in the 96 well culture dish. After 4 hours, absorbancies at 570 mµ and 600 mµ are recorded on a standard microplate reader (Dynatech). Absorbancies at 600 are subtracted from absorbancies at 570 and corresponding readings in the positive control (high concentration cisplatin/anguidine) wells are subtracted from the readings of each drug-exposed well. Each value so determined is divided by the corresponding values from the negative (vehicle) control wells (0.9% NaCl), also with positive control readings subtracted. The above result provides a crude (relatively insensitive) index of drug-induced cell death (for all cells in the culture, not distinguishing between the death of different populations of cells), which is, none-the-less, useful as an additional quality control to ensure that the microplate wells are correctly spun down on correctly-labeled ISMCVA cytospin slides.

Assay cytospin slides are prepared as previously described (Weisenthal, et al., supra (1983)), with the addition of acetaldehyde-fixed duck red blood cells (Weisenthal, et al., "Comparison of Dye Exclusion Assays with a Clonogenic Assay in the Determination of Drug-Induced Cytotoxicity," Cancer Res (1983) 43:258-264), which, in the present assays, are used primarily as a quality control to gauge the uniformity of cytospin cellular "disks" ("spots"). Post-culture slides are subjectively scored to gauge cell death as follows:

Slides are first inspected to determine which cells and clusters are tumor cells and which, if any, are normal cells, using standard cytopathologic criteria. Particular attention is given to putative capillary-associated cells, which are typically interspersed throughout the clusters and which can be recognized with practice and experience as small, often angulated cells in close proximity to one or more other cells of similar appearance. These cells are quite often somewhat hyperchromatic.

ISMCVA cytospin slide "disks" which have been stained with fast green and H/E are then scored primarily at a magnification of 40×. The slide is scanned to identify cell clusters which are largely viable and with well preserved morphology. Cell clusters should ideally contain a minimum of 20 non-capillary cells.

The negative control (0.9% NaCl vehicle) slides are scanned to determine (mentally) how slides appear in the complete absence of drug effect. The well-preserved negative control cell clusters can be referred to as "plain pancakes," to connote their relatively uniform appearance. Drug exposed cultures are examined, to select well-preserved, largely viable cell clusters. Under low power, the microaggregate is scored as to being either a "plain pancake" (if it is of largely uniform appearance) versus a "blueberry pancake," if there are multiple punctate areas staining blue-green, which, on high power, are found to be consistent with dead (fast green stained) capillary-associated cells. If desired, additional slides can be prepared and stained with an immunocytochemical method capable of specifically identifying capillary associated cells, such as staining for the CD31 antigen which is reasonably specific for endothelial cells.

If a "blueberry pancake" effect is observed in test cultures greater than that appearing in control cultures, this effect may be scored using a subjective, but standardized grading scale, such as "1+blueberries," "4+blueberries," etc. Alternatively, a microscope eyepiece grid may be superimposed over the cell clusters of interest, and the number of "blueberries" per grid unit can be counted with the aid of a standard hand tally counter. The "blueberries" could also be scored using automated image analysis systems.

Example 4

Ovarian Cancer

In a study performed on specimens of human ovarian cancer, as described in Examples 1-3, the median percent of total tumor cells in microaggregates (as opposed to being discohesive cells) at the beginning of the cultures was 80 and the median at the conclusion of the cultures was 85. The median cell cluster two dimensional area at the beginning of culture was 870 microns squared and at the conclusion of culture was 2300 microns squared. At the beginning of cell culture, 10 of all specimens were comprised entirely of discohesive single cells, and this remained 1% at the conclusion of culture. In specimens containing microaggregates, as scored at the beginning of the cell cultures, 17% of these contained predominately "loose" clusters (defined above), 78% predominately "medium-dense" clusters, and 4% predominately "tight" clusters. Corresponding percentage of assays having cell clusters at a given density at the conclusion of cell culture were 25% predominately "loose," 69% "medium-dense," and 6% "tight."

Example 5

Normal Lung

Figure 2A:
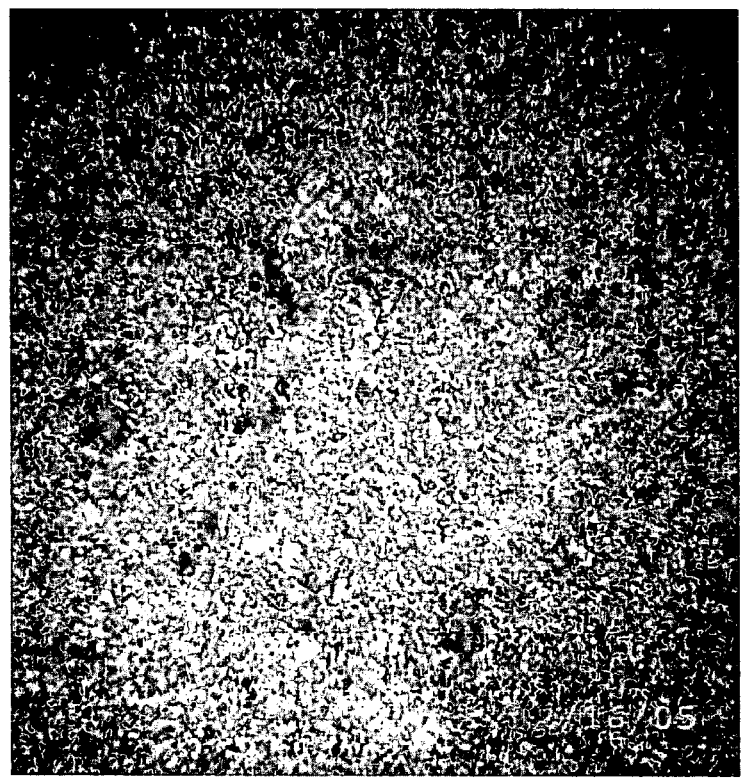
FIGS. 2A-2D are photomicrographs of various stages of preparation of the microaggregates of the invention.
Figure 2B:
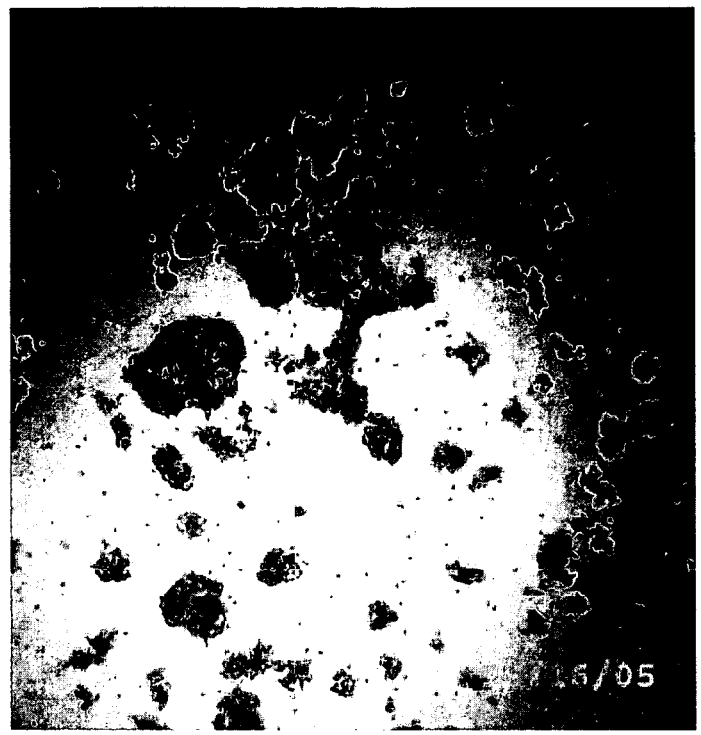
Figure 2C:
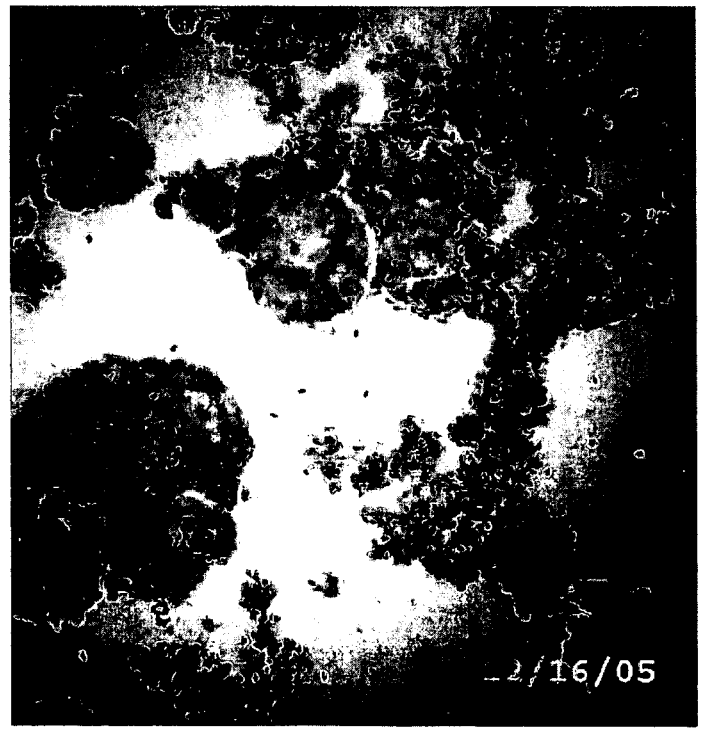
Figure 2D:
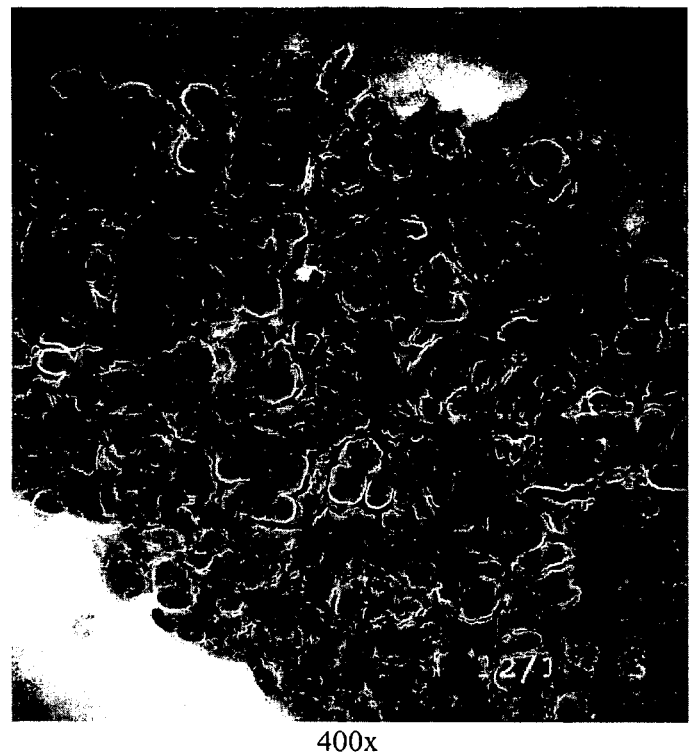

A human lung biopsy was subjected to mechanical mincing with surgical scissors, followed by digestion with collagenase/DNase. Various cell fractions were stained with fast green, cytocentrifuged, and counterstained with hematoxylin/eosin (H/E), as described in Example 1. As noted, viable cells stain pink to red (with H/E), while dead cells stain blue to green (with fast green). Acetaldehyde-fixed duck red blood cells (blue-green elliptocytes) are present as an internal standard. As shown in FIG. 2A, at 40× magnification the enzyme digestate comprises largely non-viable (blue green stained) cells, fibers, and debris, admixed with discohesive single cells, but also comprises some three-dimensional cell clusters of various sizes (original magnification 40×). The three-dimensional microclusters from the preparation shown in FIG. 2A are enriched with multiple "quickspins" 250×g, as described in Example 1, followed by concentration to a smaller volume, followed by cytocentrifugation and fast green H/E staining. The resulting microaggregates at 40× magnification are shown in FIG. 2B, at 200× magnification in FIG. 2C, and at 400× magnification in FIG. 2D.

Example 6

Neuroendocrine Tumor

Figure 3A:
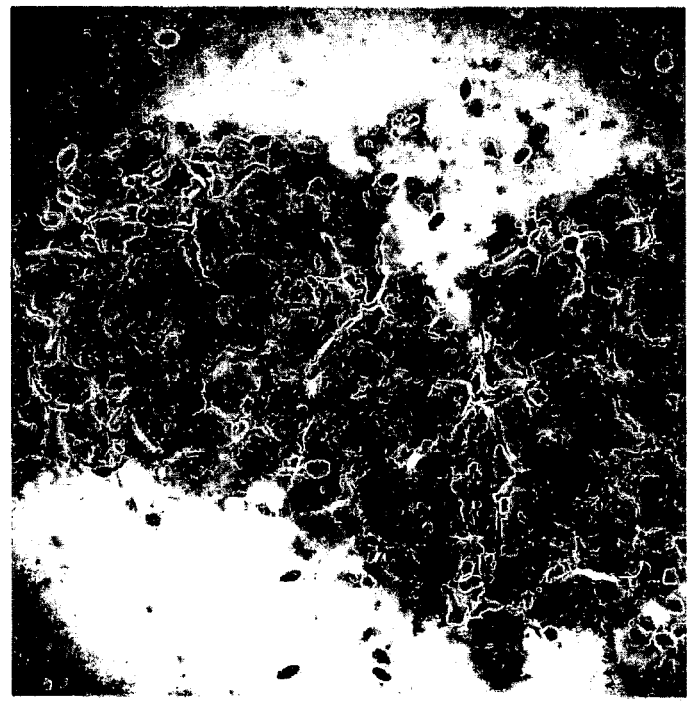
FIGS. 3A-3D are photomicrographs at 100× magnification of microaggregates of the invention that are untreated or treated with bevacizumab.
Figure 3B:
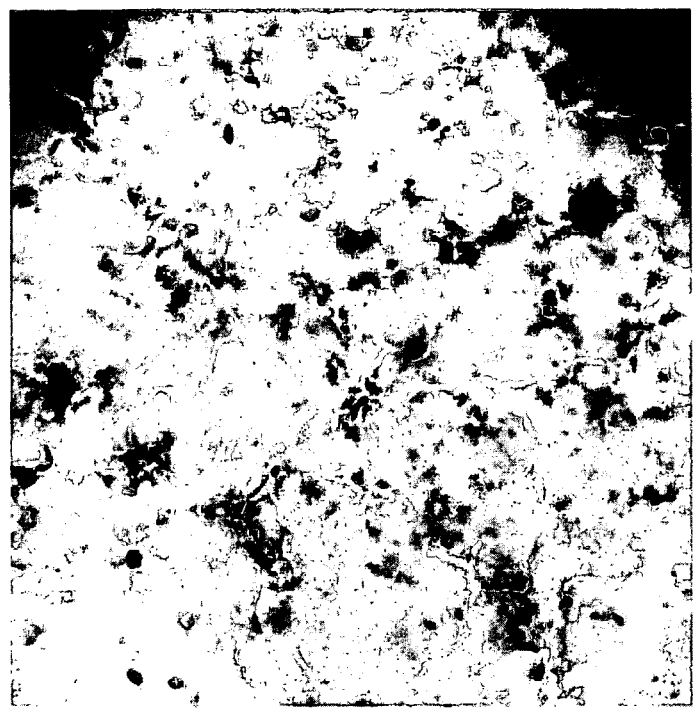
Figure 3C:
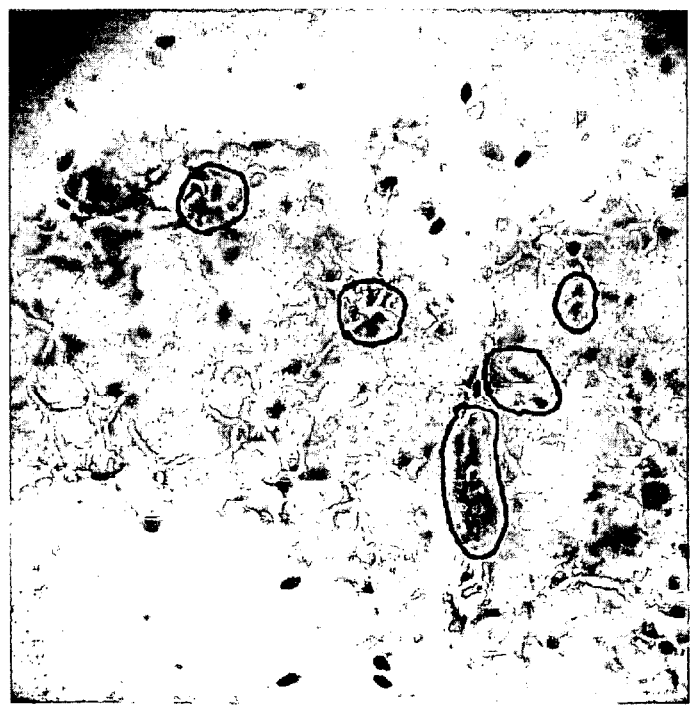
Figure 3D:
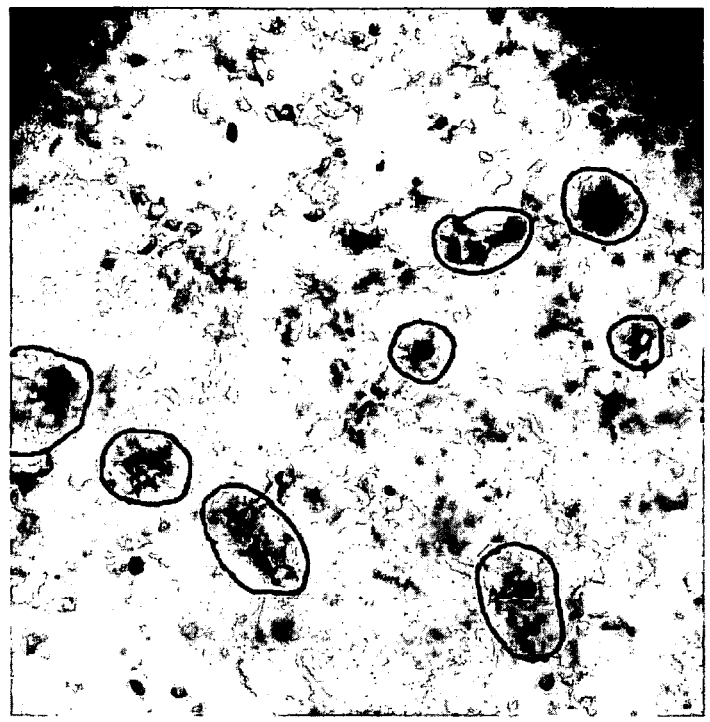
Figure 4A:
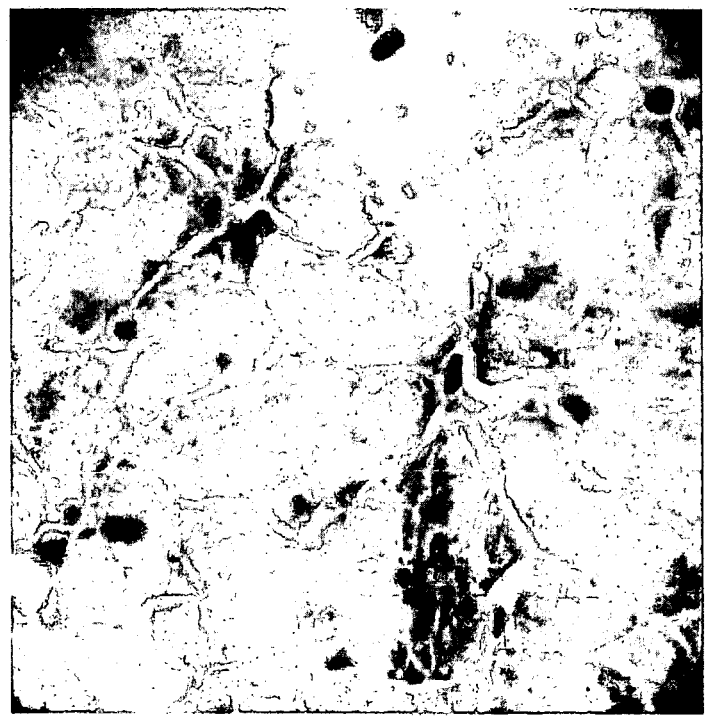
FIGS. 4A-4D are photomicrographs of the same microaggregates as shown in FIGS. 3A-3D but shown at 200× magnification.
Figure 4B:
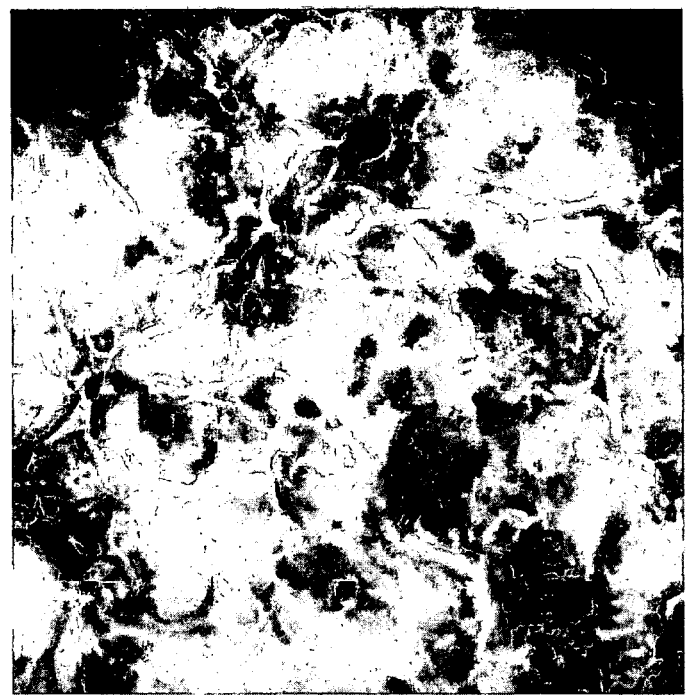
Figure 4C:
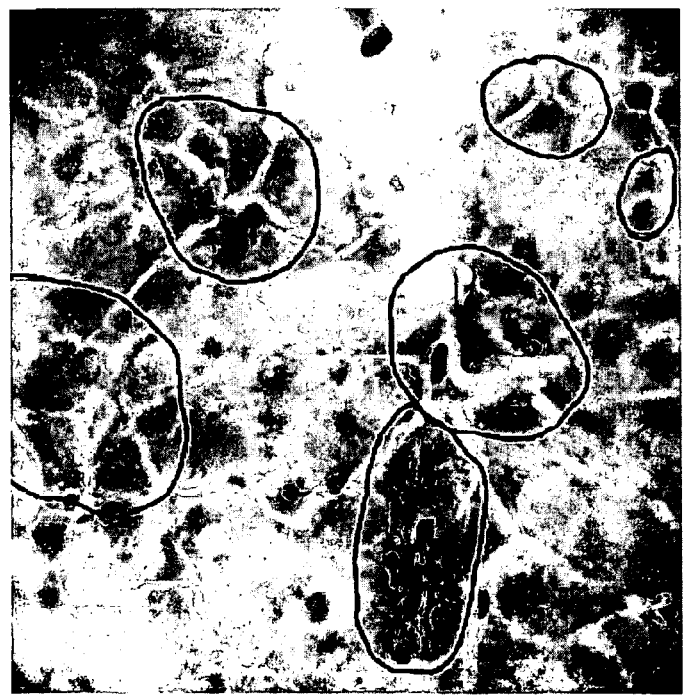
Figure 4D:
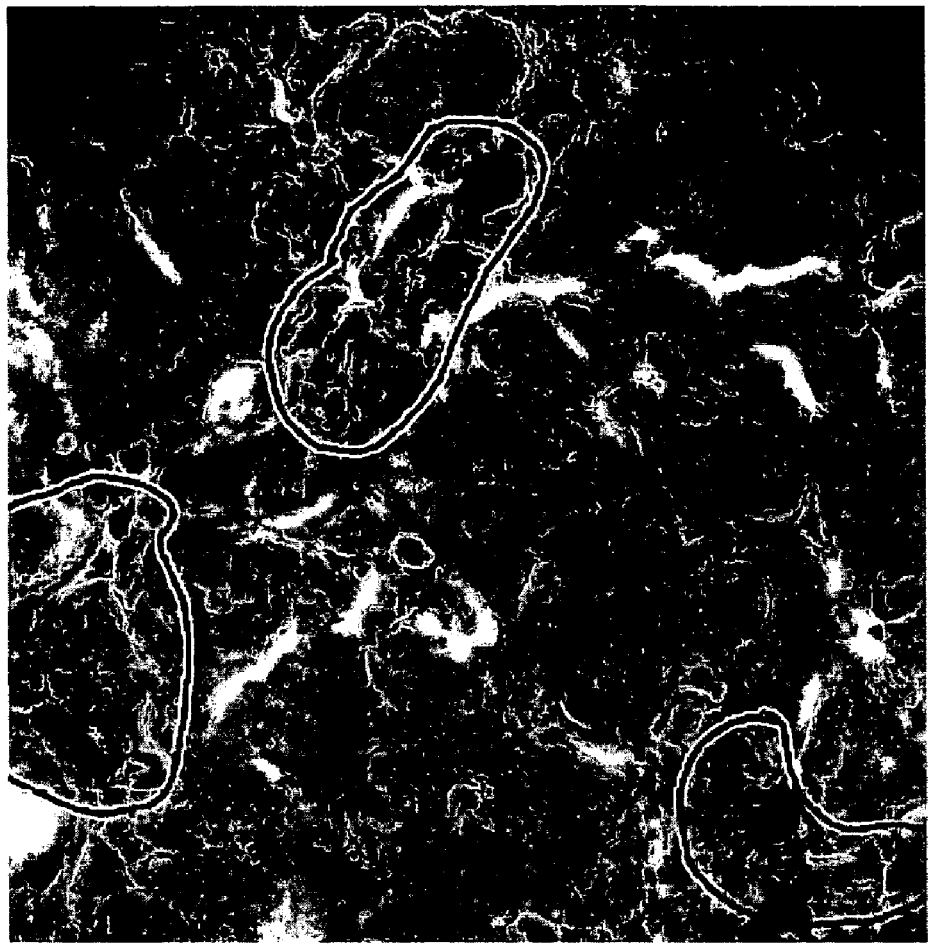

A human neuroendocrine (pulmoriary carcinoid) tumor, was biopsied, digested, enriched for microclusters and cultured for 96 hours in the absence or presence of bevacizumab generally as described in Examples 1-3. Microclusters were stained with fast green (before cytocentrifugation) and counterstained with H/E (after cytocentrifugation). As noted above, viable cells stain pink to red (with H/E), while dead cells stain blue to green (with fast green), and acetaldehyde-fixed duck red blood cells (blue-green elliptocytes) are present as an internal standard. Tumor cells are large, pale-pink staining cells and capillary-associated cells (mostly endothelial cells) are smaller, more densely red-pink stained cells, often sharply angulated. FIGS. 3A and 4A show microclusters from control culture, with mostly viable tumor cells and capillary-associated cells at 100× and 200× magnification, respectively. FIGS. 3C and 4C are the annotated forms of FIGS. 3A and 4A with capillary-associated cells are circled for ease of identification. FIGS. 3B and 4B show microclusters from bevacizumab-exposed cells at 100× and 200× magnification, respectively, and FIGS. 3C and 3D show annotated forms thereof. As shown, the tumor cells remain viable (pink stained), while most capillary-associated cells are dead (blue-green stained).

It is known that bevacizumab does not have direct effects on cells, including capillary cells, but complexes with a vascular endothelial growth factor (VEGF) produced locally by the tumor cells in the microcluster. VEGF is required for proliferation and survival of endothelial cells in bevacizumab-responsive tumors. These results show that the continuous presence of VEGF is required in order to maintain the viability of capillary associated cells. Blocking VEGF in culture with bevacizumab results in the death of VEGF-dependent capillary associated cells. Tumors which form "blueberry pancake" clusters in response to bevacizumab have a high probability of responding to clinical chemotherapy with bevacizumab, while tumors which do not form "blueberry pancake" clusters have a lower probability of responding. The assay system described also may be used to discover forms of therapy which will work against bevacizumab resistant microcapillaries.

The Invention claimed is:
1. A method to determine the endothelial cell specific effect of a treatment on viability of endothelial cells as compared to non-endothelial cells in a microaggregate, which method comprises

(a) contacting a composition comprising at least one microaggregate comprised of viable endothelial cells and viable non-endothelial cells with said treatment,
(b) adding a first indicator dye which is taken up by non-living cells and excluded by living cells;
(c) sedimenting said microaggregate onto a surface for microscopic observation;
(d) determining by microscopic observation the effect of said treatment on the viability specifically of endothelial cells in said microaggregate wherein non-viable endothelial cells are identified as hyperchromatic cells thus distinguishable from non-endothelial non-viable cells;
whereby a treatment that is determined to effect endothelial cell death is identified as successful in killing endothelial cells;
wherein steps (b) and (c) may be performed in any order.

2. The method of claim 1, wherein said first indicator dye is added to a culture of the microaggregate prior to the sedimenting step.

3. The method of claim 1, wherein said first indicator dye is added after the sedimenting step onto a surface for microscopic observation.

4. The method of claim 1, which further comprises treating the microaggregate with a second indicator dye that is not excluded by living cells.

5. The method of claim 1, wherein said first indicator dye is fast green.

6. The method of claim 4, wherein said first indicator dye is fast green and said second indicator is hematoxylin/eosin (H/E).

7. The method of claim 1, wherein the surrounding cells in the microaggregate are tumor cells.

8. A method to determine whether an agent specifically affects the viability of endothelial cells, which method comprises
treating a microaggregate comprised of at least viable endothelial cells and viable non-endothelial cells with a candidate agent;
allowing sufficient time for said agent to exert an effect;
treating the microaggregate with a first dye that is taken up by non-viable cells and excluded from viable cells; and
determining the uptake or lack of uptake of said dye by the endothelial cells and/or surrounding cells of the microaggregate wherein non-viable endothelial cells are identified as hyperchromatic cells that are thus distinguishable from other, non-endothelial non-viable cells;
whereby an agent that results in uptake of said dye in the endothelial cells of the microaggregate, is determined to be an agent that specifically affects the viability of endothelial cells.

9. The method of claim 8, which further comprises, prior to the determining step, treating said microaggregate with a solution of a second dye, wherein said solution effects greater visibility of said first dye.

10. The method of claim 9, wherein said first dye is fast green and said second dye is hematoxylin/eosin (H/E).

* * * * *